United States Patent [19]

Burge et al.

[11] Patent Number: 5,147,561

[45] Date of Patent: Sep. 15, 1992

[54] DEVICE FOR SAMPLING AND STRIPPING VOLATILE CHEMICALS WITHIN WELLS

[76] Inventors: Scott R. Burge, 8869 S. Myrtle, Tempe, Ariz. 85331; Russell Burge, 21140 Covina Hills Rd., Covina, Calif. 91724

[21] Appl. No.: 612,613

[22] Filed: Nov. 13, 1990

Related U.S. Application Data

[63] Continuation-in-part of Ser. No. 383,340, Jul. 24, 1989, abandoned.

[51] Int. Cl.[5] .................. B02D 19/00; E21B 49/08
[52] U.S. Cl. .................. 210/747; 73/1 G; 73/19.1; 73/863.02; 73/863.23; 166/264; 166/265; 210/170; 210/188; 436/39; 436/178
[58] Field of Search .................. 166/53, 205.5, 264, 166/265, 267, 336; 175/58–60; 73/1 G, 19.01, 19.1, 61 R, 863.01, 863.02, 863.21, 863.23, 863.86, 864.34, 864.63, 864.74, 863.24; 210/170, 188, 747, 767, 321.5; 203/10, 143, 97; 422/80, 23.1; 55/36, 46, 158, 159

[56] References Cited

U.S. PATENT DOCUMENTS

| | | | |
|---|---|---|---|
| 4,003,257 | 1/1977 | Fletcher et al. | 55/197 |
| 4,630,677 | 12/1986 | Jakob | 166/264 |
| 4,717,473 | 1/1988 | Burge et al. | 166/264 |
| 4,764,272 | 8/1988 | Fox, Sr. | 210/188 |
| 4,821,585 | 4/1989 | Kempe | 73/863.23 |
| 4,857,473 | 8/1989 | Margaritz et al. | 73/863.23 |
| 4,922,747 | 5/1990 | Wall | 73/19.01 |
| 5,010,776 | 4/1991 | Lucero et al. | 73/863.23 |

FOREIGN PATENT DOCUMENTS

3126648  1/1983  Fed. Rep. of Germany ..... 73/61 R

Primary Examiner—Robert A. Dawson
Assistant Examiner—Joseph Drudge
Attorney, Agent, or Firm—Jordan Meschkow; Don J. Flickinger; Lowell W. Gresham

[57] ABSTRACT

A sampling device for sealed positioning within the casing of a well contains a stripping chamber for stripping a ground water sample of its volatile compounds at or near the point of collection. In one embodiment, the stripping chamber includes a piston which is raised above the top surface of the sample to create a head space, and an injector for injecting inert gas into the sample, causing the volatile compounds to be released into the head space, whereupon they exit the chamber via a vapor outlet duct leading out of the well. In a second embodiment, the stripping chamber includes a tube having a sidewall formed of a semi-permeable membrane, and an injector which injects an inert gas into the bore of the tube. The device may also include a sensor mounted within the stripping chamber, and a valve for directing a calibration gas into the chamber.

27 Claims, 4 Drawing Sheets

DEVICE FOR SAMPLING AND STRIPPING VOLATILE CHEMICALS WITHIN WELLS

CROSS-REFERENCE TO RELATED APPLICATION

This is a continuation-in-part of my earlier application, entitled "Device for In-Situ Stripping of Volatile Chemicals from Ground Water for the Purposes of Analytical Measurements", which was filed on Jul. 24, 1989, and assigned U.S. Pat. Ser. No. 383,340, now abandoned.

BACKGROUND OF THE INVENTION

1. Field of the Invention

This invention relates to a device for collecting chemicals for analysis.

More particularly, this invention relates to a device for sampling and stripping volatile chemicals from ground water.

In a further and more specific aspect, the instant invention concerns a sampling unit for placement in a well casing to allow in-situ, real time analysis of volatile compounds in ground water.

2. Description of the Prior Art

Various devices are known for sampling ground water. One such device, which was disclosed in U.S. Pat. No. 4,717,473 to Burge et al., comprises a sorption column mounted underneath a pumping unit, whereby the pumping unit draws ground water through the sorption unit to allow analysis of various chemical parameters in the water. A special packer is provided for mounting the pumping unit and sorption column in a well casing and for preventing exchange of gases between the atmosphere and the ground water.

The above-mentioned device represents a substantial improvement over prior art samplers, since the packer eliminates numerous sources of errors usually associated with ground water sampling. For instance, it prevents foreign matter from dropping into the well. In addition, it prevents atmospheric oxygen from increasing the dissolved oxygen content of the water, which may result in the oxidation and/or reduction of several chemical species encountered in ground waters. Most importantly, it prevents the volatization of organic compounds, and allows for the collection of a time-averaged sample which is representative of the true contamination of the aquifer.

Nevertheless, the device disclosed in the '473 patent suffers from a number of shortcomings which make real-time analysis of samples impractical. For instance, the device fails to take into account the fact that most analytical methods require volatile compounds in a matrix of inert gas rather than water. Thus, any sample collected on the sorption column would still have to be transported to a location outside the well, where it would then be stripped of its volatile compounds and analyzed using conventional methods. At least some of these compounds will have been lost during transport, thereby reducing the precision and reproducibility of any test results. In addition, the device does not provide any means for calibrating analytical instruments within the well.

It would be highly advantageous, therefore, to remedy the foregoing and other deficiencies inherent in the prior art.

Accordingly, it is an object of the present invention to provide a device for allowing in-situ, real-time analysis of ground water in a well.

Another object of the invention is the provision of a sampling device having means for removing volatile compounds from ground water while the water is still within the well casing.

And another object of the invention is to provide a method of calibrating analytical instruments within the casing of a well.

And still a further object of the invention is the provision of a method and apparatus, according to the foregoing, which allow simple and accurate ground-water analysis at a relatively low cost.

SUMMARY OF THE INVENTION

Briefly, to achieve the desired objects of the instant invention in accordance with the preferred embodiments thereof, a sampling device is provided for collecting a sample of a selected medium, such as ground water, and for stripping the sample of its volatile compounds at or near the point of collection. The device comprises a housing which is positioned in the casing of a well by an inflatable packer or other sealing means which prevents volatile compounds from escaping from the well casing to the atmosphere. The housing contains a sealed chamber having a valved inlet port through which the medium enters. Stripping means are provided in the chamber for volatizing and releasing the volatile compounds from the medium, whereupon they exit the chamber via a vapor outlet duct leading out of the well.

In one embodiment of the invention, the stripping means are in the form of a piston which is used to create a head space above the upper surface of the medium, and an injector which injects an inert gas into the medium to volatilize the compounds and release them into the head space. A pumping unit is provided for controlling reciprocation of the piston, to draw the medium into the chamber at the beginning of the sampling operation, and to force the medium out during a flushing operation prior to taking new samples.

In a second embodiment of the invention, the stripping means are in the form of a tube having a sidewall formed of a semi-permeable membrane, and an injector which injects an inert gas into the bore of the tube. The inlet port to the sealed chamber is located outside of the tube, while the vapor outlet duct communicates with the bore of the tube. When the medium enters the chamber, the volatile compounds diffuse through the semi-permeable membrane, become entrained in the inert gas in the bore, and are carried out through the outlet duct to a location where they can be tested.

Analysis of the sample can be carried out in a number of different ways. The volatilized compounds may simply be transported through the outlet duct to an instrument or instruments located outside the well. Alternatively, analysis may be performed inside the device itself, using a sensor or sensors mounted within the sealed chamber or the outlet duct. In the latter case, the injector may deliver a calibration gas to the interior of the sealed chamber to permit calibration of the sensor. In applications which do not require stripping, the medium can be directed out of the sealed chamber and to a sorptive column which can be removed and tested outside of the well using conventional methods. In addition, a waste reservoir is provided for collecting waste material which is discharged from the sealed chamber during the flushing operation.

BRIEF DESCRIPTION OF THE DRAWINGS

The foregoing and further and more specific objects and advantages of the instant invention will become readily apparent to those skilled in the art from the following detailed description of the preferred embodiments thereof taken in conjunction with the drawings in which.

DETAILED DESCRIPTION OF THE PREFERRED EMBODIMENTS

Figures 1, 2:
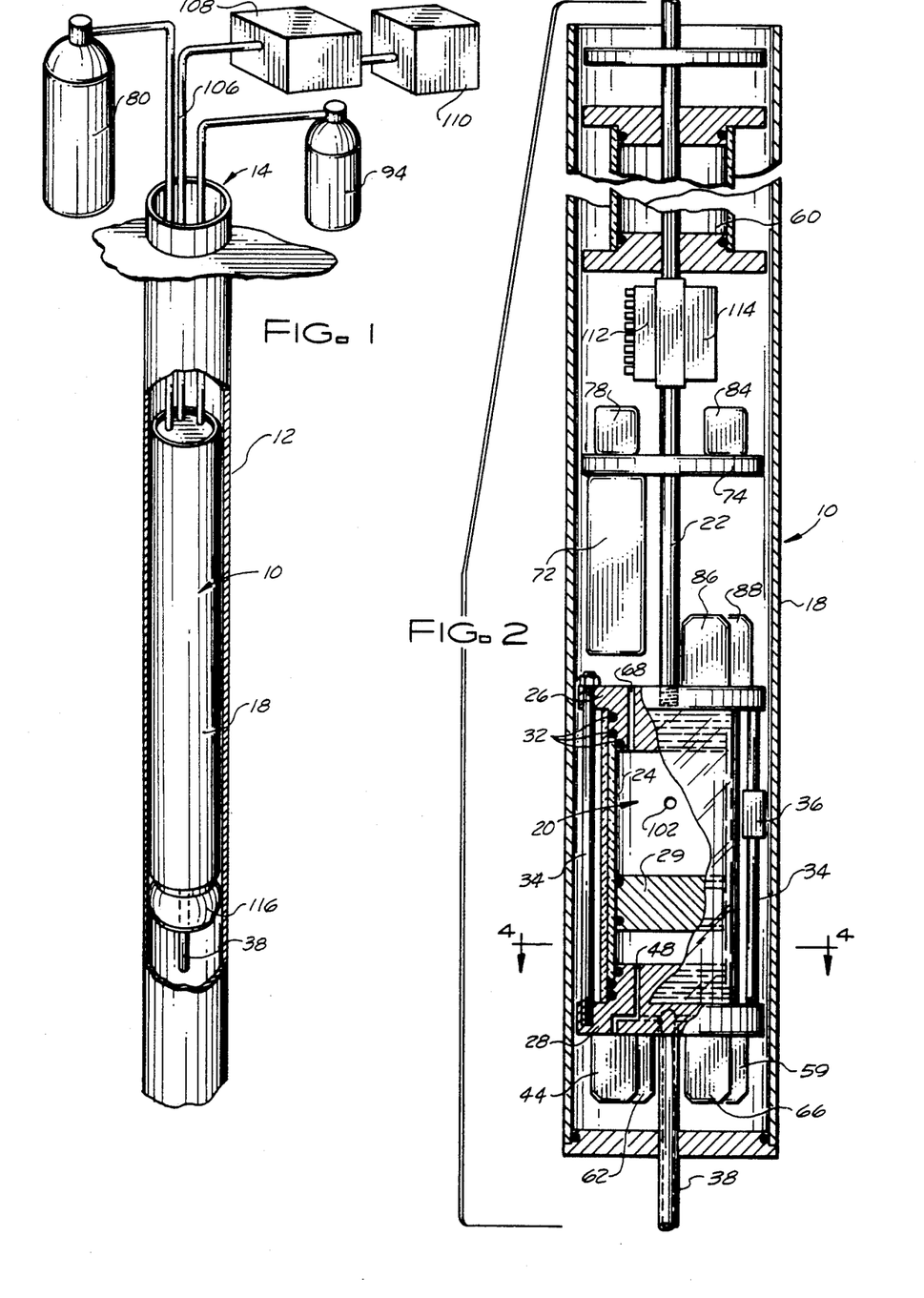
FIG. 1 is a perspective view showing the sampling device of the present invention positioned within the casing of a well.
FIG. 2 is a fragmentary sectional view of the sampling device of FIG. 1, with portions broken away, and with tubing and wiring removed for greater clarity.

Turning now to the drawings in which like reference characters indicate corresponding elements throughout the several views, attention is first directed to FIG. 1, which shows a sampler device according to the present invention, indicated in its entirety by the numeral 10, positioned in the casing 12 of a ground-water well 14. An inflatable packer 16, which is shown here as a separate module depending from the housing 18 of the device 10, provides a tight seal between the housing 18 and the casing 12, thus preventing volatile compounds in the well 14 from escaping to the atmosphere. Alternatively, a dedicated mounting system in which the packer 16 surrounds and is integral with the housing 18 may also be used. In yet another alternative, the casing 12 may be specially designed to closely receive the housing 18, so that packer 16 is unnecessary.

The internal components of the device 10 will now be described with reference to FIGS. 2-5. A tightly sealed, cylindrical stripping chamber 20 is supported in the housing 18 by an elongated rigid rod 22 extending through the housing 18. The chamber 20 comprises a precision glass tube 24 having a top plug member 26 mounted in its upper end and a bottom plug member 28 mounted in its lower end. A piston 29 is mounted for reciprocation in the tube 24. Also captured between the plugs 26, 28, and protectively surrounding the glass tube 24 is a clear polycarbonate tube 30. A plurality of O-rings 32 between each of the tubes 24, 30 and the top and bottom plug members 26, 28 ensure that the chamber 20 is air and water-tight. Structural support is provided by a pair of stainless steel tie rods 34 extending between the plugs 26, 28. A sensor 36 for detecting the level of water in the chamber 20 may be mounted on one of the rods 34.

Figures 3, 4, 5, 6:
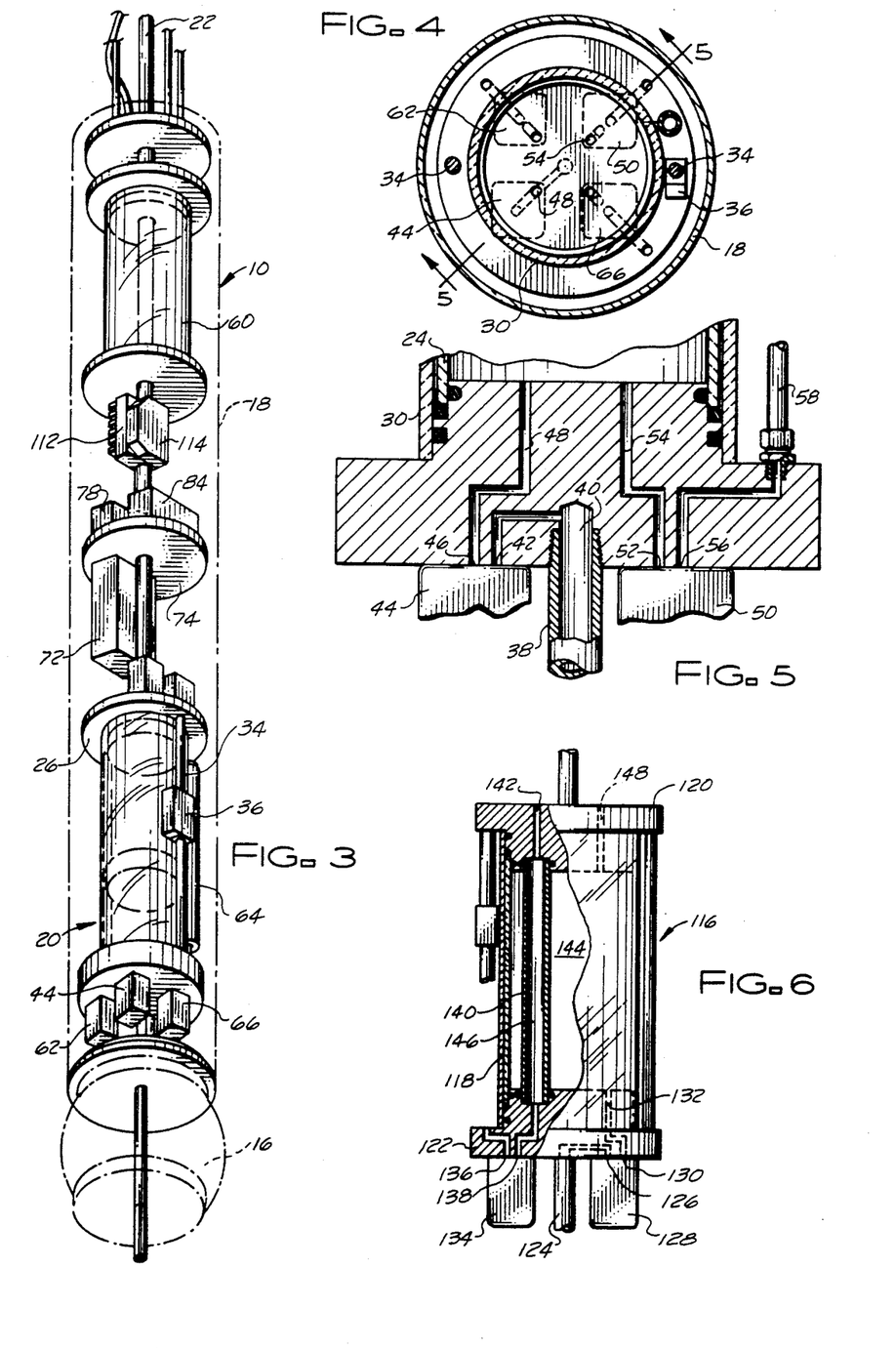
FIG. 3 is a perspective view showing the internal elements of the sampling device, with external elements indicated in phantom.
FIG. 4 is sectional view taken through line 4—4 of FIG. 2.
FIG. 5 is a fragmentary sectional view taken through line 5—5 of FIG. 4.
FIG. 6 is a perspective (?) view showing an alternative embodiment of the stripping chamber in the sampling device.

Ground water is admitted to the stripping chamber 20 by an intake tube 38 which depends from the bottom plug member 28 and 11 extends into the water. The outlet end 40 of the intake tube 38 communicates with the inlet port 42 of a normally closed, two-way solenoid valve 44 mounted on the underside of the plug 28. The outlet port 46 of the valve 44 communicates with a flow passage 48 which extends through the plug 28 and opens into the chamber 20.

Also mounted on the underside of the plug 28 is another normally closed, two-way solenoid valve 50 having an inlet port 52 for receiving flow from an outlet passage 54 leading from the chamber 20, and an outlet port 56 communicating with an outlet conduit 58 leading to a waste reservoir 60 mounted on support rod 22 in the upper portion of the housing 18. Another normally closed, two-way solenoid valve 62 on the underside of the bottom plug member 28 controls the flow of liquid from the stripping chamber 20 to a sorptive column 64, while still another normally closed, two-way solenoid valve 66 controls the flow of an inert purging gas into the chamber. For the sake of simplicity, the various inlet and outlet passages and tubing associated with valves 62 and 66, as well as the conduit 58 leading from valve 50 to the waste reservoir 60, have not been shown in FIGS. 2 and 3. However, the layout of such passages and tubing will be evident to the technician of ordinary skill in the art, especially in light of the schematic drawings in FIG. 7-13, which will be discussed shortly in connection with the operation of the device.

Figure 13:
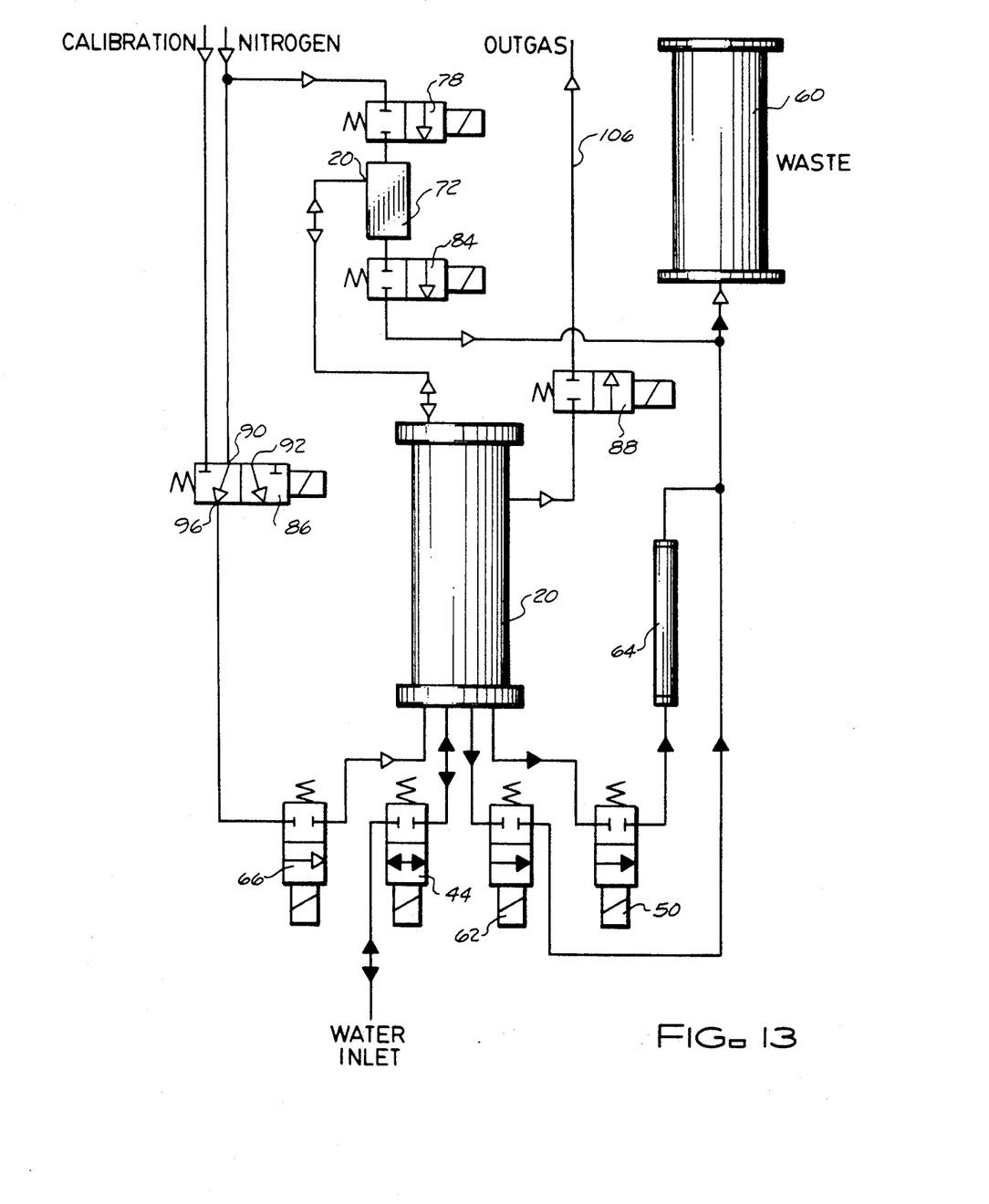
FIG. 13 is a flow diagram of the sampling device of the present invention.

Returning now to FIG. 2, with additional reference to FIG. 13, the upper plug member 26 of the stripping chamber 20 includes a through-passage 68 which communicates with the suction port 70 of a suction pump 72, which is mounted on the underside of a circular plate 74 supported on rod 22 above the stripping chamber 20. The pump 72 also includes an inlet port 76 which is controlled by a normally closed, two-way direct solenoid inline valve 78 and connected to a source of compressed gas 80, which is located at the surface of the well 14 and is preferably the same inert gas (i.e. Nitrogen) used in the stripping chamber 20. The exhaust port 82 of the pump 72 is controlled by another two-way solenoid valve 84 supported on the circular plate 74. The pump 72 may be eliminated in those cases where the hydrostatic pressure in the well 14 is sufficient to force water into the stripping chamber 20 without assistance.

Also mounted on the upper plug member 26 of the stripping chamber 20 are a three-way solenoid valve 86 and a two-way solenoid valve 88. The three-way valve 86 includes a first inlet port 90 communicating with the source of inert purging gas 80, a second inlet port 92 communicating with a source of calibration gas 94, and an outlet port 96 communicating with the inlet port 98 of two-way valve 66 located below the bottom plug member of the chamber 20. The two-way valve 88 includes an inlet port 100 communicating with a vapor outlet port 102 formed through the side wall of the stripping chamber 20, and an outlet port 104 communicating with an outlet tube 106 leading to various analytical devices 108, 110, such as sorptive tubes, chemical sensors, gas chromatographs, mass spectrographs and the like. Once again, the various tubes and flow passages leading to and from the valves 78, 84, 86 and 88 have been eliminated from FIG. 2 for the sake of simplicity. The electronic controls for all of the valves are located in a terminal block 112 carried on support rod 22 above the pump 72. A controller 114 for the water level sensor 36 is also coupled to the terminal block 112.

In a second embodiment of the invention, the stripping chamber 20 is replaced by an alternate stripping chamber 116, illustrated in FIG. 6. The alternate stripping chamber 116 comprises a tubular sidewall 118 having a top plug member 120 carried in its upper end and a bottom plug member 122 carried in its lower end. As in the first embodiment, a water intake tube 124 depends from the bottom plug member 122, and communicates at its outlet end with the inlet port 126 of a normally closed, two-way solenoid valve 128. The outlet port 130 of the valve 128 communicates with a flow passage 132 extending through the plug 122 and opening into the chamber 116.

Another normally closed, two-way solenoid valve 134 mounted on the underside of the bottom plug 128 includes an inlet port 136 for receiving inert gas from a source located outside the well, and an outlet port 138 which communicates with the bore of a tube 140 extending through the chamber 116. The opposite end of the tube 140 communicates with a vapor outlet passage 142 formed in the upper plug member 120. Thus, the space surrounding the tube 140 effectively defines a first subchamber 144 for containing ground water drawn through the intake tube 124, while the bore of the tube 140 defines a second subchamber 146 for containing inert gas admitted by valve 134. The tube 140 is formed from a semi-permeable membrane which allows volatile organic contaminants in the ground water to diffuse into the column of inert gas in the second subchamber 142.

The top plug member 120 of the stripping chamber 116 also includes a through-passage 148 which communicates with the suction port of pump 72 in the same manner as through passage 68 of the first embodiment. Also supported on the top plug member 120, although not shown, are a two-way solenoid valve and a three way solenoid valve, for performing the same functions as valves 86 and 88 in the first embodiment. Similarly, the bottom plug member 122 includes an additional pair of two-way solenoid valves which perform the same functions as valves 50 and 62 in the first embodiment, but which are obstructed from view in FIG. 6.

OPERATION OF THE DEVICE

First Embodiment

The sampling device 10 can be operated in several different modes, depending on the type of analysis to be performed and the location of the test instruments. In a first mode, it can be used to strip a ground water sample of volatile organic contaminants, and to transfer the volatilized contaminants to test instruments 108, 110 located outside of the well 14. In a second mode, it can be used to simply transfer the ground water to a sorptive column 64. In a third mode, it can be used to calibrate a sensor 150 located in the stripping chamber 20 itself.

Figure 7:
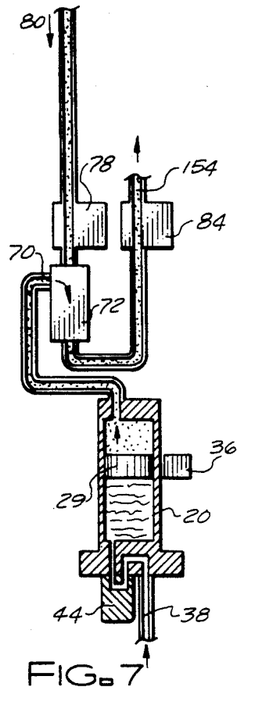
FIG. 7 is a schematic view showing the pattern of flow through the device during a filling cycle.
Figure 8:
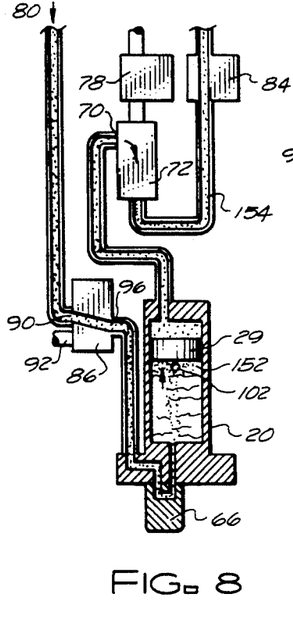
FIGS. 8 and 9 are schematic views showing the pattern of flow through the device during the two stages of a purging cycle.
Figure 9:
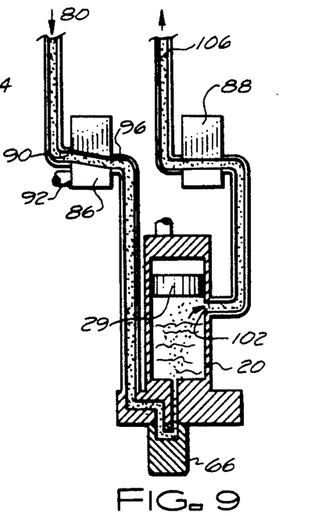

FIGS. 7-9 illustrate a sequence of steps involved in the first mode of operation. FIG. 7 illustrates the step of filling the stripping chamber 20 with ground water. This is accomplished by opening the water intake valve 44, as well as the compressed gas supply valve 78 and exhaust valve 84 of the pump 72. This creates a negative pressure at the suction port 70 of the pump 72, causing piston 29 to be drawn upwardly in the stripping chamber 20. The piston continues to rise, drawing the ground water with it, until the sensor 36 indicates that a desired water level has been reached.

In response to a signal from the sensor 36, valves 44 and 78 close, and valve 66 opens, while three-way valve 86 moves into a position wherein the first inlet port 90 is aligned with the outlet port 96, resulting in the configuration shown in FIG. 8. This configuration allows a burst of inert purging gas from source 80 to be injected into the chamber 20, forcing the piston 29 above outlet port 102 and creating a head space 152 between the top surface of the ground water and the bottom of the piston 29. In this configuration, as in the configuration shown in FIG. 7, gas in the upper portion of the chamber 20 which is displaced by the upward motion of the piston 29 is drawn through the suction port 70 of the pump 72 and exhausted to the atmosphere via an exhaust duct 154.

After the head space 152 has been created, the inert gas continues to bubble into the chamber 20 through valve 66, and valve 88 is opened, as shown in FIG. 9. This allows the volatile contaminants in the groundwater to be released into the head space 152, and transmitted through outlet tube 106 to a sorptive tube assembly and/or other analytical instruments 108, 110 located at the surface or within the well itself.

Figure 10:
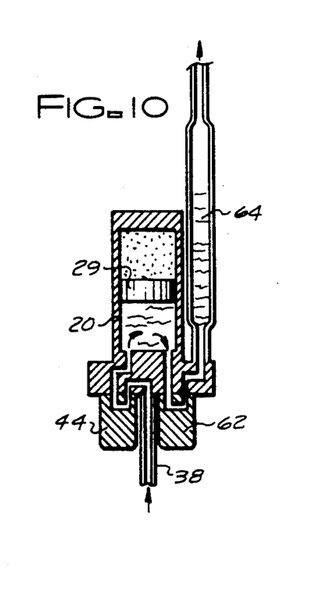
FIG. 10 is a schematic view showing the flow being directed to a sorptive column; 11

FIG. 10 illustrates the second mode of operation, which may be used to perform tests in which purging is not required. This mode is performed simply by opening valves 44 and 62, allowing the ground water to enter chamber 20, and then exit immediately into sorptive tube 64. It has been assumed, for the purposes of this illustration that the hydrostatic forces in the well 14 are sufficient to force the water into the sorptive tube 64, without assistance from the pump 72. If this is not the case, it would be necessary to first fill the chamber 20 using the filling step shown in FIG. 7, and then to produce a positive pressure by opening the compressed gas supply valve 78 and closing the exhaust valve 82 of the pump 72. The positive pressure would force the piston 29 to move downwardly in the chamber 20, thus assisting the flow of the ground water into the sorptive tube 64.

Figure 11:
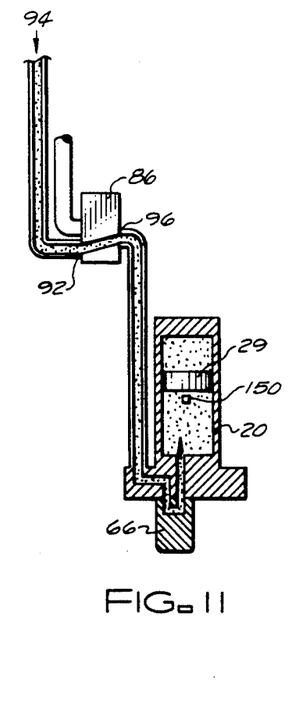
FIG. 11 is a schematic view showing the pattern of flow during a calibration cycle.

The third mode of operation is illustrated in FIG. 11. In this mode, a gas sensor 150 is provided in a recess in the sidewall of the stripping chamber 20. The sensor 150 is calibrated by opening two-way valve 66 and moving the three-way valve 86 into the position wherein second inlet port 92 is aligned with outlet port 96, thus allowing a stream of calibration gas from source 94 to be injected into the chamber 20. All other valves in the system are closed. Since the composition of the calibration gas is known, the user can easily calibrate the sensor 150 by comparing the reading of the sensor with the known composition of the calibration gas and adjusting the sensor to agree with the correct value. This operation makes it possible to perform a head space analysis on volatilized compounds from the ground water while the compounds are still in the chamber 20. As a result, many of the losses associated with transporting the compounds to outside test instruments are eliminated. Alternatively, the sensor 150 may be located in the gas outlet duct 106 rather than in the chamber 20 itself.

Figure 12:
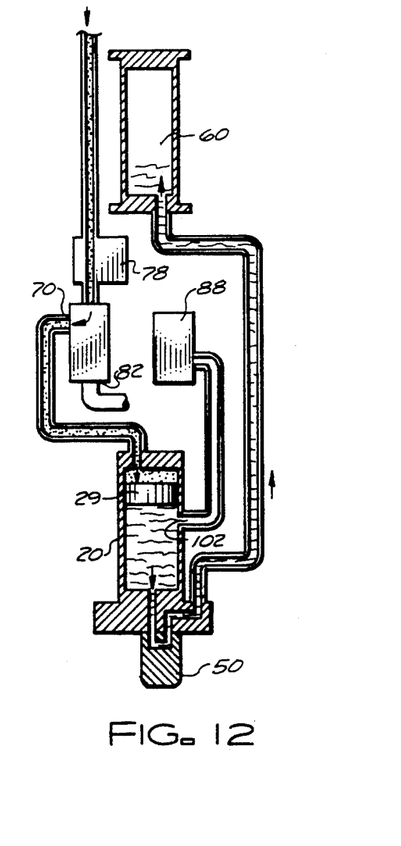
FIG. 12 is a schematic view showing the pattern of flow during a flushing cycle.

Finally, FIG. 12 shows a flushing cycle which can be used 11 after any of the operations described above to rid the chamber 0 of stagnant water before beginning a new operation. First, the piston 29 is raised to its highest position and the chamber 0 filled to its capacity using the procedure of FIG. 7. Then, the exhaust valve 82 of the pump 72 is closed, producing a positive pressure at port 70, which forces the piston 29 downwardly. At the same time, the valve 88 controlling vapor outlet port 102 is closed, and the waste water outlet valve 50 is opened, allowing the water to be expelled into waste reservoir 60, in the upper portion of the housing 18.

OPERATION OF THE DEVICE

Second Embodiment

Operation of the second embodiment is virtually identical to the first embodiment, except that step two of the first mode of operation, shown in FIG. 11, is eliminated since there is no piston with which to create a head space. To strip the water of its volatile components, it is simply necessary to open vapor inlet valve 134 and vapor outlet valve 88, so that volatile contaminants in the ground water can diffuse through the semi-permeable membrane 140 and become entrained in the outflowing column of inert gas.

Various modifications and variations to the embodiments herein chosen for purposes of illustration will readily occur to those skilled in the art. For instance, it is clear that the device need not be limited to the sampling of liquids such as ground water, but can also be used to sample gaseous media. To the extent that such variations and modifications do not depart from the spirit of the invention, they are intended to be included within the scope thereof which is assessed only by a fair interpretation of the following claims.

Having fully described and disclosed the instant invention and alternately preferred embodiments thereof in such clear and concise terms as to enable those skilled in the art to understand and practice the same, the invention claimed is:

1. A device adapted for sealed placement in the casing of a well for sampling a selected medium containing volatile compounds, said device comprising:
   a) a housing for insertion into said casing;
   b) a sealed chamber within said housing;
   c) inlet means communicating with said chamber for allowing said medium to enter said chamber, and including valve means for selectively controlling entry of said selected medium into said sealed chamber;
   d) stripping means in said chamber for volatizing and releasing said volatile compounds from said selected medium;
   e) vapor outlet means communicating with said chamber for transporting the volatilized compounds to an analysis unit;
   f) sensor means for detecting when the medium in said sealed chamber has reached a predetermined level; and
   g) control means operatively connected to said sensor means and said valve means for closing said valve means when said medium has reached said level.

2. A device according to claim 1, further comprising a pumping unit for drawing said medium into said sealed chamber.

3. A device according to claim 1, wherein said medium comprises a liquid having a top surface.

4. A device according to claim 3, wherein said stripping means comprises:
   a) means for creating a head space above the top surface of said liquid in said sealed chamber; and
   b) injection means for injecting an inert gas into said liquid to volatilize said compounds and release said compounds into said head space.

5. A device according to claim 4, wherein said outlet means comprises an outlet port located above said inlet means.

6. A device according to claim 5, wherein said means for creating a head space comprises a piston mounted for reciprocation within said sealed chamber, from a first position intermediate said inlet means and said outlet port to a second position above said outlet port, in response to forces exerted on said piston by gases injected through said injection means.

7. A device according to claim 4, further comprising:
   a) first gas delivery means for delivering an inert gas to said injection means;
   b) second gas delivery means for delivering a calibration gas to said injection means; and
   c) control means for selectively coupling either said first gas delivery means or said second gas delivery means in communication with said injection means.

8. A device according to claim 1, wherein said stripping means comprises:
   a) a semi-permeable membrane dividing said sealed chamber into a first subchamber communicating with said inlet means and a second subchamber communicating with said vapor outlet means; and
   b) an injector communicating with said second subchamber to inject an inert gas into said second subchamber;

whereby said volatile compounds in said medium in said first subchamber diffuse through said membrane and are entrained in said inert gas as said inert gas travels through said second chamber 9. A device according to claim 1, further comprising:
   a) a waste reservoir located within said housing; and
   b) medium outlet means communicating with said sealed chamber and said waste reservoir for transporting said medium from said chamber to said waste reservoir.

10. A device according to claim 9 wherein said medium outlet means comprises valve means for selectively controlling exit of said medium from said sealed chamber.

11. A device according to claim 1, further comprising analyzing means in said sealed chamber for analyzing gas composition within said chamber.

12. A method of sampling a selected medium containing volatile compounds, said method comprising the steps of:
   a) placing a sampling device into the casing of a well containing said selected medium, said sampling device including:
      i) a housing,
      ii) a sealed chamber within said housing, and
      iii) inlet means communicating with said sealed chamber for allowing said selected medium into said chamber;
   b) providing a seal between said housing and said well casing to prevent volatile compounds from escaping from the well to the atmosphere;
   c) drawing said medium through said inlet means into said sealed chamber;

d) volatizing and releasing said volatile compounds from said medium while said medium is in said chamber including the step of injecting an inert gas into said sealed chamber; and e) analyzing said volatile compounds.

13. A method according to claim 12, wherein said step of volatizing and releasing further comprises the substep of creating a head space above said medium, whereby said volatile compounds are released into said head space.

14. A method according to claim 12, wherein said step of analyzing said volatile compounds comprises the step of providing a sensor within said housing to obtain real-time, in situ data.

15. A method according to claim 14, further comprising the step of calibrating said sensor in situ prior to obtaining said data.

16. A method according to claim 15, wherein said step of calibrating said sensor comprises the substeps of:

a) injecting a calibration gas having a known composition into said sealed chamber and in communication with said sensor;

b) obtaining a reading from said sensor and comparing the reading of said sensor with the known composition of said calibration gas; and c) adjusting said sensor such that the reading agrees with said known composition.

17. A device adapted for sealed placement in the casing of a well for sampling a selected medium containing volatile compounds, said device comprising:

a) a housing for insertion into said casing;

b) a sealed chamber within said housing;

c) inlet means communicating with said chamber for allowing said medium to enter said chamber;

d) stripping means in said chamber for volatizing and releasing said volatile compounds from said selected medium;

e) vapor outlet means communicating with said chamber for transporting the volatized compounds to an analysis unit;

f) a sorptive tube located within said housing; and g) medium outlet means communicating with said sealed chamber and said sorptive tube for transporting said medium from said chamber to said sorptive tube.

18. A device according to claim 17, further comprising a pumping unit for drawing said medium into said sealed chamber.

19. A device according to claim 17, wherein said medium comprises a liquid having a top surface.

20. A device according to claim 19, wherein said stripping means capable of stripping comprises:

a) means for creating a head space above the top surface of said liquid in said sealed chamber; and b) injection means for injecting an inert gas into said liquid to volatilize said compounds and release said compounds into said head space.

21. A device according to claim 20, wherein said outlet means comprises an outlet port located above said inlet means.

22. A device according to claim 21, wherein said means for creating a head space comprises a piston mounted for reciprocation within said sealed chamber, from a first position intermediate said inlet means and said outlet port to a second position above said outlet port, in response to forces exerted on said piston by gases injected through said injection means.

23. A device according to claim 20, further comprising:

a) first gas delivery means for delivering an inert gas to said injection means;

b) second gas delivery means for delivery a calibration gas to said injection means; and c) control means for selectively coupling either said first gas delivery means or said second gas delivery means in communication with said injection means.

24. A device according to claim 17, wherein said stripping means comprises:

a) a semi-permeable membrane dividing said sealed chamber into a first subchamber communicating with said inlet means and a second subchamber communicating with said vapor outlet means; and b) an injector communicating with said second subchamber to inject an inert gas into said second subchamber;

whereby said volatile compounds in said medium in said first subchamber diffuse through said membrane and are entrained in said inert gas as said inert gas travels through said second chamber.

25. A device according to claim 17, further comprising:

a) a waste reservoir located within said housing; and b) medium outlet means communicating with said sealed chamber and said waste reservoir for transporting said medium from said chamber to said waste reservoir.

26. A device according to claim 25, wherein said medium outlet means comprises valve means for selectively controlling exit of said medium from said sealed chamber.

27. A device according to claim 17, wherein said medium outlet means comprises valve means for selectively controlling exit of said medium from said sealed chamber.

* * * * *

UNITED STATES PATENT AND TRADEMARK OFFICE
CERTIFICATE OF CORRECTION

PATENT NO. : 5,147,561
DATED : 15 September 1992
INVENTOR(S) : Scott R. Burge, Russell Burge It is certified that error appears in the above-identified patent and that said Letters Patent is hereby corrected as shown below:

In Column 7, line 2, delete "11".

In Claim 20, line 53, delete "capable of stripping".

Signed and Sealed this

Fourteenth Day of September, 1993

Attest:

BRUCE LEHMAN

*Attesting Officer*   *Commissioner of Patents and Trademarks*